United States Patent [19]

Hunter et al.

[11] Patent Number: 5,608,171

[45] Date of Patent: *Mar. 4, 1997

[54] DISTRIBUTED, UNATTENDED WASTEWATER MONITORING SYSTEM

[76] Inventors: Robert M. Hunter; Frank M. Stewart, both of 320 S. Willson Ave., Bozeman, Mont. 59715

[*] Notice: The term of this patent shall not extend beyond the expiration date of Pat. No. 5,423,226.

[21] Appl. No.: 360,300

[22] Filed: Dec. 21, 1994

Related U.S. Application Data

[63] Continuation-in-part of Ser. No. 164,146, Dec. 9, 1993, Pat. No. 5,423,226, which is a continuation-in-part of Ser. No. 153,178, Nov. 16, 1993, Pat. No. 5,406,828.

[51] Int. Cl.⁶ ........................................................ G01F 1/44
[52] U.S. Cl. ........................................... 73/861.63; 73/215
[58] Field of Search ........................... 73/865.8, 170.17, 73/170.21, 215, 861.63; 340/870.02, 870.03, 870.16, 870.28

[56] References Cited

U.S. PATENT DOCUMENTS

| | | | |
|---|---|---|---|
| 3,719,081 | 3/1973 | Lynn et al. | 73/215 |
| 4,022,059 | 5/1977 | Schontzler et al. | 73/215 |
| 4,367,652 | 1/1983 | Venuso | 73/215 |
| 4,665,743 | 5/1987 | Masniere et al. | 73/170.17 |
| 4,940,976 | 7/1990 | Gastouniotis et al. | 340/870.02 |
| 5,194,860 | 3/1993 | Jones et al. | 340/870.28 |

*Primary Examiner*—Kenneth A. Wieder
*Assistant Examiner*—Harshad Patel

[57] ABSTRACT

A distributed, unattended wastewater monitoring system that uses advances in low-energy signal processing and distributed microelectromechanical systems and that involves wireless interrogation of distributed, low-power, normally-off sensors. In a preferred embodiment, a plurality of flow-meter stations and at least one rain gauge station are networked through a base station for storm water discharge of infiltration-inflow monitoring. Wireless transceivers are used to transmit radio signals into and out of a sewer manhole.

22 Claims, 7 Drawing Sheets

DISTRIBUTED, UNATTENDED WASTEWATER MONITORING SYSTEM

STATEMENT AS TO RIGHTS IN INVENTIONS MADE UNDER FEDERALLY-SPONSORED RESEARCH AND DEVELOPMENT

This invention was made with Government support under Small Business Innovation Research Contract No. DAAH01-94-C-R131 awarded by the Advanced Research Projects Agency, a component of the U.S. Department of Defense. The Government has certain rights in the invention.

CROSS-REFERENCES TO RELATED APPLICATIONS

This is a continuation in part of application Ser. No. 08/164,146, filed Dec. 9, 1993, now U.S. Pat. No. 5,423,226 which is a continuation in part of application Ser. No. 08/153,178, filed Nov. 16, 1993 now U.S. Pat. No. 5,406,828.

BACKGROUND OF THE INVENTION

The background of the invention is set forth in two parts: the field of the invention and the description of related art.

1. Field of the Invention

This invention relates to a method and apparatus for wastewater flow monitoring. In particular, it relates to wastewater flow metering and sampling.

2. Description of Related Art

The invention disclosed herein provides improvements to the state of the art and particularly to the inventions disclosed in U.S. Pat. No. 4,799,388 by Hunter, Jan. 24, 1989, entitled "Apparatus and Technique for Metering Liquid Flow"; U.S. Pat. No. 4,896,542 by Hunter Jan. 30, 1990, entitled "Portable Wastewater Flow Meter"; and U.S. Pat. No. 5,199,306 by Hunter, Apr. 6, 1993, entitled "Method and Apparatus for Metering Flow in Closed Conduits that Surcharge". The disclosure of the aforementioned U.S. patents are incorporated by reference herein as if fully set forth.

Those patents disclose a variety of primary flow elements and secondary flow elements. In some embodiments, the primary flow elements comprise constrictions configured to cause simultaneous filling of the constriction and the upstream pipe upon increasing flow rate. In other disclosed embodiments, the primary flow elements comprise constrictions configured to cause filling of the constrictions and/or the upstream pipe before the modular limit of the device is reached. The disclosed secondary flow elements utilize a variety of means to transmit and sense the level and pressure changes caused by the primary flow elements.

A variety of commercially-available devices may be used for wastewater monitoring. One example is the Sigma 950 Series Open Channel Flow Meter manufactured by American Sigma. It is a secondary element that can be used with such primary elements as weirs, flumes, and nozzles. A rain gauge and an automatic sampler can be connected to the secondary element. Data can be downloaded from this secondary element via a hand-held memory module, a telephone modem, or a personal computer.

Another example is the Isco 3200 Series Open Channel Flow Meter manufactured by Isco, Inc. Data can be downloaded from this secondary element via a laptop computer, a short haul modem, a telephone modem, or a data switch.

Some of these flowmeters, as well as flowmeters manufactured by Marsh McBirney, Inc. and Stevens Inc. measure flow rate by directly measuring velocity and depth. Thus, no primary element is required.

The Streamline 800SL Portable Liquid Sampler manufactured by American Sigma is an example of a portable sampler. It is described in U.S. Pat. No. 4,660,607, the disclosure of which is incorporated herein as if fully set forth. Other examples are the Isco Model 6000 Sampler and the Isco 3700 Series Portable Wastewater Samplers manufactured by Isco, Inc.

Other background material is presented in a report entitled "Distributed Unattended Storm Water Discharge Monitoring—Phase I Final Technical Report", dated October 1994, by Yellowstone Environmental Science, Inc., 320 S. Willson Ave., Bozeman, Mont. 59715, at the e-mail address 74203.3640@compuserv.com. The disclosure in that report is incorporated by reference herein as if fully set forth.

Limitations of prior art systems include the need for hard-wired connections among system components. For example, in order to interrogate a secondary unit that is installed in a sewer manhole, the heavy manhole cover must be removed and an RS-232 cable connected between the secondary element and the portable computer being used to interrogate the secondary element. Prior art systems are also limited in that accurate flow metering in closed conduits that surcharge is not possible and a separate rain gauge must be hard-wire connected to each secondary element.

SUMMARY OF THE INVENTION

The present invention provides a method and apparatus for distributed, unattended wastewater monitoring. The invention uses advances in low-energy signal processing and distributed microelectro-mechanical systems to provide a very-large-scale distributed systems in which (1) the sensing dynamic range is minimal and (2) the data rate to or from any particular sensor or device is low. The invention involves wireless interrogation of distributed, low-power sensors; a broadcast scheme and devices for the broadcast to and from distributed, normally-off sensors; and integrated antennas.

At a minimum, the system is comprised of two elements: a monitoring of flowmeter station, comprising a first wireless transmitter/receiver (transceiver), and a base station comprising a second transceiver. In a another embodiment, the system comprises a flowmeter station, a rain gauge station and a base station. In a preferred embodiment, a plurality of flowmeter stations and at least one rain gauge station are networked through a base station.

In a preferred embodiment the monitoring of flowmeter stations are installed in sewer manholes. Sewer manholes are typically underground vaults that generally have the shape of a vertical, right cylinder. Typically, the top end of a manhole has the shape of an eccentric truncated cone. A cast-iron manhole cover rests on the top of the truncated cone and provides access to the manhole from the surface. Some manhole covers have at least one hole (termed a pick hole) in them to facilitate their removal.

In one embodiment, each flowmeter comprises at least a secondary element. In other embodiments each flowmeter is comprised of two elements: a primary element and a secondary element. The primary element comprises a constriction in a closed conduit that produces pressures in liquid flowing through it that are related to the rate of flow of the liquid. In one embodiment, the constriction is configured by reference to the patents noted above to cause essentially simultaneous filling of the constriction and the conduit upstream from it upon increasing flow rate. In other disclosed embodiments, the primary flow elements comprise constrictions configured to cause filling of the constriction and/or the upstream pipe before the modular limit of the device is reached. For the purposes of this disclosure, the term "modular limit" means the point at which an increase in the water level downstream from a constriction (tail water depth) begins to affect the water level upstream from the constriction.

The primary element (constriction) can be installed in a pipe of any size or shape. The throat of the primary element can be almost any shape, but the top of the throat is preferably flat. Design of the constriction involves selection of a conventional critical depth flume design and then adding a top sill. The elevation of the bottom surface of the top sill may be chosen to effectively lower the top of the throat so that the throat fills with liquid at the same flow rate as the upstream pipe fills with liquid on increasing flow rate. Alternatively, the elevation of the bottom surface of the top sill may be chosen so as to cause either the throat or the upstream pipe to fill first on increasing flow rate.

In a preferred embodiment, the primary element has an entrance section that causes the flow stream to converge as it enters the throat. Preferably, the entrance section has a shape that is an eccentric, truncated cone.

As disclosed in U.S. Pat. Nos. 4,799,388, 4,896,542 and 5,199,306, pressure sensors are used to quantify pressures produced in the liquid as it flows through the primary element. In a preferred embodiment, the pressure sensors are low-power, normally-off microelectromechanical devices supplied by Lucas Nova Sensor.

A first wireless transmitter/receiver is attached to each secondary element. The attachment may be integral (e.g., on the same printed circuit board or integrated circuit) or attachment may be by means of a hard-wired connection. The first transceiver transmits signals which are characterized by a first output power value. It is adapted to transmit and receive radio frequency (RF) signals.

In one embodiment, the first transceiver's antenna is a conventional antenna. In another embodiment, the antenna is electrically coupled and mechanically attached to the manhole cover by means of a magnet. In another embodiment, an antenna is installed (flush-mounted) in a hole in a manhole cover. In yet another embodiment, the cover itself is used as the antenna.

In a preferred embodiment, a conventional automatic sampler is attached to and adapted so as to be activated by the secondary element. The sampler is adapted to take either time-weighted or flow-weighted composite samples and/or to take grab samples.

In an alternative embodiment, the monitoring station comprises a parameter monitor which may be attached to the secondary element or take its place. The parameter monitor provides direct in-stream measurement of physical and chemical parameters, such as pH, conductivity, temperature, turbidity, dissolved oxygen (DO) and/or oxygen reduction potential (ORP).

Preferably, the base station comprises a second wireless transceiver and a computer. The second transceiver has an antenna and is adapted to transmit and receive RF signals. The transmitted signals are characterized by a second transmission power value. The base station may either be permanently located (e.g., in the office of a wastewater system manager or consulting engineer) or it may be mobile (e.g., in a vehicle).

In this embodiment, rain gauge stations are distributed throughout the area that contribute wastewater to sewers that convey it to the manholes in which the flowmeters are located. Each rain gauge station is connected to a transmitter that has an antenna and that is adapted to transmit RF signals.

In an alternative embodiment, a single rain gauge is hard wired to the base station computer. All rain gauges or rain gauge stations produce a signal that is proportional to a certain amount of precipitation. For example, tipping bucket rain gauges typical produce a signal each time 0.01 inch of rainfall has occurred.

A wireless communication link is either continuously or intermittently established between the base station and each flowmeter and/or each rain gauge station. The link is preferably established intermittently by means of signals transmitted by the base station. The first transceivers are adapted to transmit radio signals of at least two transmission power values. When transmission is from a flowmeter in a manhole with a cover having a standard (approximately one-inch diameter) hole therethrough, a transmission power of at least 0.05 milliwatts is used. When transmission is from a flowmeter in a manhole with a nonstandard (holeless) cover, a transmission power of at least 5 milliwatts is used.

The wireless communication link may be either a two-stage subsystem or a one-stage subsystem. In two-stage subsystems, the first stage comprises a means of transmission between a transceiver located below ground surface in a monitoring site manhole and a nearby transceiver located above ground level. These transceivers are identified as the manhole unit and the roadside unit, respectively. The second stage of the wireless link comprises a means of transmission between the roadside unit and the base station.

The first stage is required to transmit signals through solid objects (either a cast iron manhole cover or tens of feet of soil), and to operate on a lightweight battery supply which can be easily carried up and down a manhole ladder. The second link is required to transmit through an atmospheric path for relatively long distances.

In one embodiment, the first stage is preferably a frequency modulated (FM) spread-spectrum radio. FM spread spectrum radios operate in the ultra-high frequency (UHF) radio region. The FCC allows license-free transmissions of up to 1 watt in three designated bands within the UHF region for commercial spread-spectrum communication. The spread spectrum technology was developed by the military to provide multiple users with a noise and interference-resistant system for both voice and data communication.

Commercially-available devices range from low-cost single-chip transmitters to sophisticated programmable transceivers. An example of a single-chip transmitter is the Motorola frequency-shift-keyed (FSK) MC2833. A compatible receiver chip is the Motorola MC3362. A set of these chips costs about $3 in quantities of 100. Use of these chips requires design and fabrication of a custom circuit board with numerous auxiliary components. An example of the next step up in complexity and cost is the Maxim MAX 2401 variable-output power transmitter chip which allows a complete spread-spectrum transceiver to be built on five integrated circuit chips for a cost of about $40. Some design work would be required to build a practical system around these components. At the other end of the price range, Proxim Corporation sells a fully-programmable, RS-232 compatible OEM transceiver board for about $350 in quantities of 100.

A variety of technologies have potential for use in the second-stage link. These techniques include cellular telephone networks, digital data networks, two-way pager networks, satellite, private spread-spectrum FM transceivers, and private narrow-band FM transceivers. Some of these technologies which are currently being developed have the potential of eliminating the need for a first-stage link when they become commercially available.

In one embodiment, cellular telephone technology is used for digital data transmission by replacing the conventional telephone handsets with special wireless modems. The transmission mode of cellular telephone systems is similar to spread-spectrum FM, and uses the frequency band around 890 MHZ. Current cellular systems were developed primarily for voice communication, and are not ideal for data transmission since digital data is more sensitive to noise and interference than voice. Digital transmission rates with cellular telephones are limited to around 1,200 to 2,400 baud with presently available systems. Hardware costs for this technology are currently around $1,000 per site. Network costs are dependent on the number and length of transmissions, and distance between base station and monitoring sites.

A new digital cellular system is under development in the U.S. by an eight-company consortium. This system, CDPD (cellular digital packet data) shows excellent potential for data transmission, but will not be available in most U.S. cities for several years. Hardware and network costs are expected to be similar to the conventional cellular systems.

In another embodiment, digital data networks are used. Two of the major companies offering this type of service are RAM Mobile Data (owned by McCaw Cellular Communications) and Ardis. These networks provide two-way communication between users and a base site. The users are linked by wireless transmission to a regional antenna, and the signals are transmitted to the base station over conventional telephone wire lines. Ardis advertises coverage of 90 percent of the U.S. population with 1,400 regional stations. Wireless transmission is on the 800 MHz band, and data is sent in packets.

Typical users include stock traders who make transactions via laptop computers and small branch stores that are linked to a central office. These systems are set up to charge a low transmission price (less than $1 per transmission), but a relatively high base station price (about $1,500 per month per base station). Hardware costs are about $400 per wireless site and $1,200 per base station.

In yet another embodiment, conventional FM transceivers made especially for data transmission are used. These devices have ranges of 20 miles or more and transmission rates in excess of 9,600 baud. These devices require site-specific FCC licenses which typically require about two months for approval. In order to reduce the potential for interference between users, these transceivers are assigned to a particular frequency and location, and thus cannot be moved from city to city without relicensing. Cost of the transceivers is about $1,200 each.

In a preferred embodiment, two-way pager networks are used as a second stage or as a single stage. Two-way pager networks are an emerging technology group which are expected to become operational on a limited basis around mid-1995. In July, 1994, ten companies bought licenses from the FCC to provide two-way data transmission services on the 900 MHz band. Communications are in near real time, with expected delays of 1 minute maximum. The systems will employ a sophisticated digital technology which will allow the wireless sites to broadcast strings of data in very short, high-powered bursts. This technology results in a wireless site unit which is advertised to operate for up to 30 days on a single AAA battery, with a range of up to 5 miles. Motorola Corporation has developed a handheld wireless transceiver for use with all of the networks. This device, code named "Tango" is reportedly expected to retail for around $325 with a display screen. Network charges are not available at the time of this report, but they are expected to be competitive with existing one-way pager systems.

Yet another embodiment incorporates satellite communication. Satellite communication links are available for users who are sponsored by Federal, state, or local government agencies via the GOES (Geostationary Operational Environmental Satellites) system. This system allows communication during predetermined times of about one-minute duration each 3 to 4 hours. Transmission is one-way only, thus and does not support the standard RS-232 two-way protocols. Due to the complexity and constraints of this system, GOES would probably be a feasible communication choice only in situations where other communication methods are not available.

At least two private satellite systems (Teledesic and Iridium) are under consideration which, if realized, would provide user-friendly, two-way data communication. These systems are not expected to be operational before 1998.

Another embodiment incorporates high-power FM spread spectrum data transceivers. By using directional Yagi antennas mounted above ground level, one manufacturer advertises a transmission range of up to 15 miles with transceivers costing about $1,200 each. Commercially available devices are not designed for energy-efficient burst transmissions or low-power standby mode, and thus have high supply power requirements. A typical commercially-available device operating for 14 days would require a rechargeable battery weighing about 40 pounds.

The present invention provides a variety of advantages over the prior art. One object of the invention is to eliminate the need to remove a heavy manhole cover to interrogate a secondary element. Another object is to eliminate the need to stand in a heavily-trafficked roadway or for an antenna to protrude into the roadway in order to interrogate a wastewater monitor. Another object is to allow automatic sampling of a wastewater stream in response to rainfall events and/or increases in flow rate. Another object is to allow wireless communication in a network of monitoring stations. Another object is to minimize the power consumption of radio transmissions to and from flowmeter stations in manholes. Yet another object is to provide minimal obstruction to the transport of sand and gravel along a sewer invert. Further objects and advantages of the invention will become apparent from consideration of the drawings and the ensuing description of it.

BRIEF DESCRIPTION OF THE DRAWINGS

The features of the invention will be better understood by reference to the accompanying drawings which illustrate presently preferred embodiments of the invention.

In the drawings.

Figure 1:
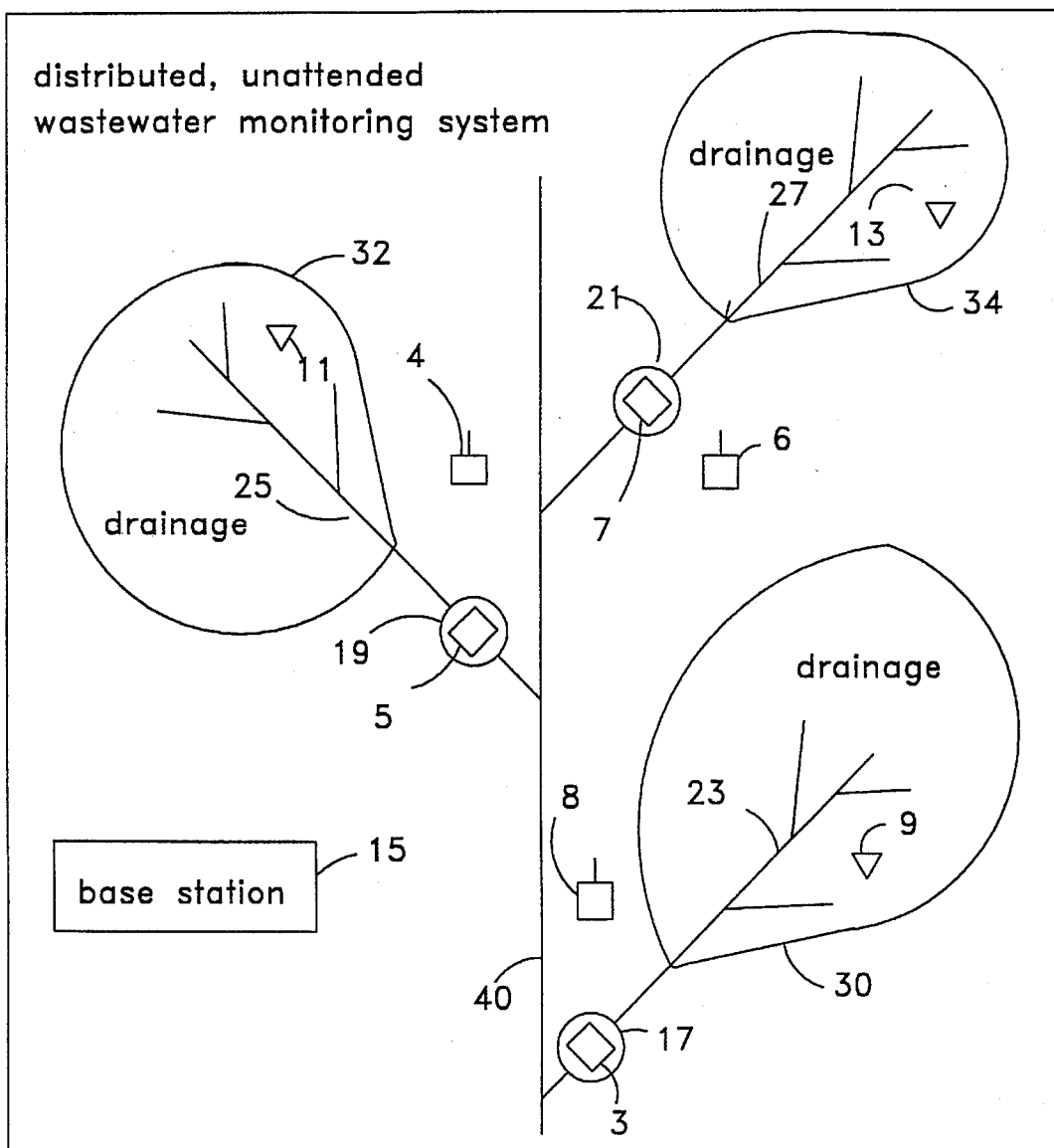
FIG. 1 is highly schematic diagram of the distributed, unattended wastewater monitoring system.

The following reference numerals are used to indicate the parts of the invention on the drawings:

1 distributed, unattended wastewater monitoring system
3 monitoring of flowmeter station
4 relay transceiver
5 monitoring of flowmeter station
6 relay transceiver
7 monitoring of flowmeter station
8 relay transceiver
9 rain gauge station
11 rain gauge station
13 rain gauge station
15 base station
17 manhole
19 manhole
21 manhole
23 main sewers
25 main sewers
27 main sewers
30 subarea, drainage
32 subarea, drainage
34 subarea, drainage
40 interceptor sewer, water course
42 first secondary element
44 first wireless transmitter/receiver, transceiver
45 first antenna
46 step
48 step
50 primary element
52 automatic sampler of parameter monitor
54 cover
56 standard hole
57 rain gauge
60 bucket rain gauge
62 second transceiver
63 rain gauge datalogger
64 second antenna
70 personal computer
72 display device, monitor
74 input device, keyboard
76 rain gauge datalogger
78 rain gauge
80 third transceiver
82 third antenna
90 primary element, flowtube
92 entrance section
94 throat section
96 short exit section
98 extended exit section
102 entrance
103 exit
105 centerline, longitudinal axis of rotation
107 centerline, axis of rotation

DESCRIPTION OF THE PREFERRED EMBODIMENTS

Reference is now made to FIG. 1 which is a highly schematic block diagram of a representative embodiment of distributed, unattended wastewater monitoring system 1. In a preferred embodiment, system 1 comprises monitoring of flowmeter stations 3, 5, and 7, rain gauge stations 9, 11, and 13 and base station 15. Monitoring of flowmeter stations 3, 5, and 7 are located in manholes 17, 19, and 21 respectively on main sewers 23, 25, and 27. Main sewers 23, 25, and 27 collect wastewater from subareas or drainages 30, 32, and 34. The rainfall amount and rates in subareas or drainages 30, 32, and 34 are characterized by rain gauge stations 9, 11, and 13, respectively. Main sewers 23, 25, and 27 discharge to interceptor sewer or water course 40.

Figure 2:
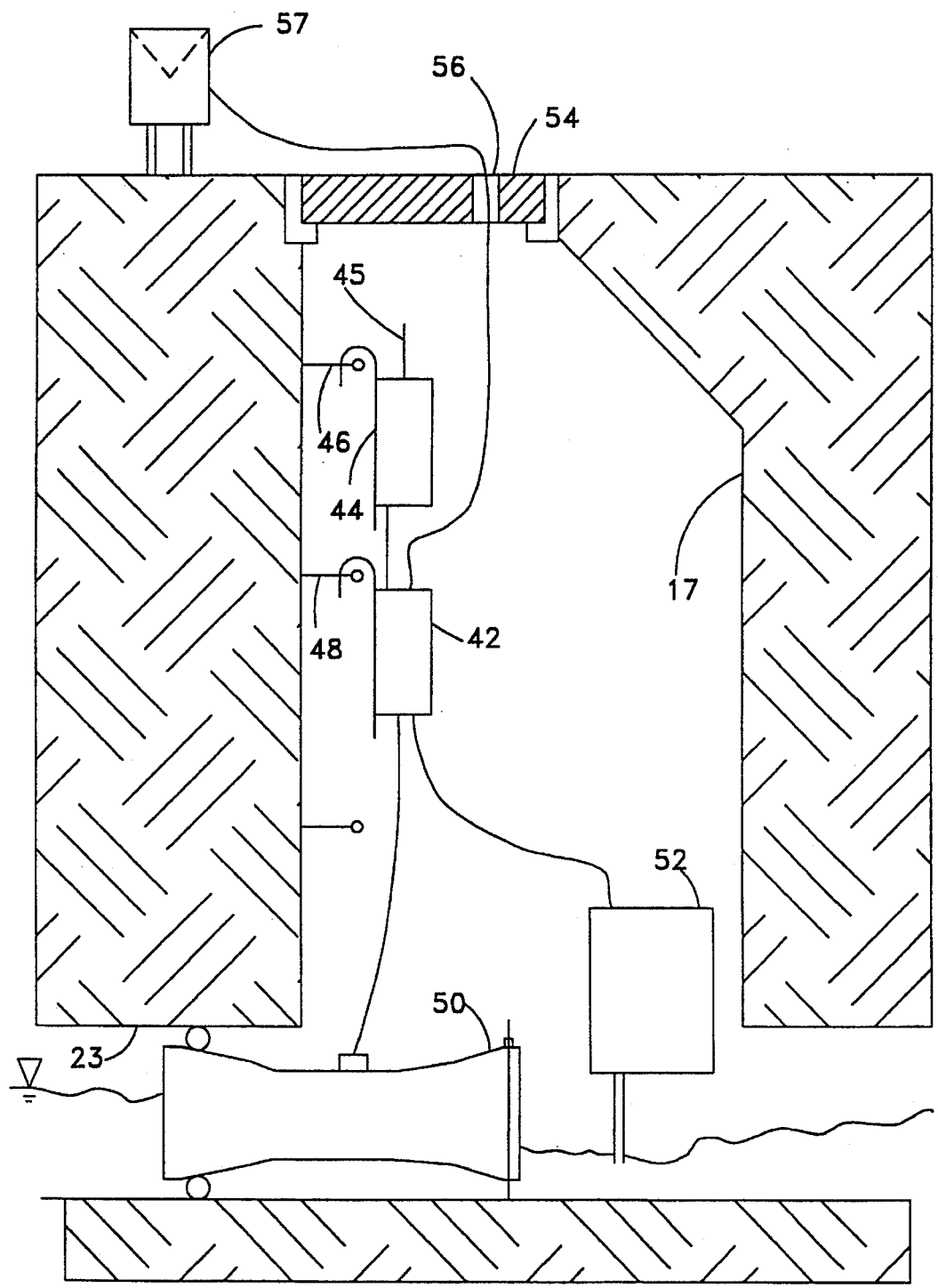
FIG. 2 is a schematic diagram of a flowmeter station.

Reference is now made to FIG. 2 which is a schematic, diagram of a representative embodiment of monitoring of flowmeter station 3 which is located on sewer 23 in manhole 17 as shown in FIG. 1. Monitoring of flowmeter stations 5 and 7 are similar to monitoring of flowmeter station 3. Monitoring of flowmeter station 3 comprises first secondary element 42 and first wireless transmitter/receiver or transceiver 44 and first antenna 45. Secondary element 42 and transceiver 44 hang on steps 46 and 48 of manhole 17, respectively. Monitoring flowmeter station 3 may also comprise primary element 50 and automatic sampler or parameter monitor 52. Access to manhole 17 is by lifting cover 54 that is provided with standard hole 56. In an alternate embodiment, flowmeter station also comprises rain gauge 57.

In an alternative embodiment, first transceiver 44 is the first stage in a two-stage wireless link to base station 15 as shown in FIG. 1. The second stage of the wireless link is provided by relay transceivers 4, 6, and 8.

Figure 3:
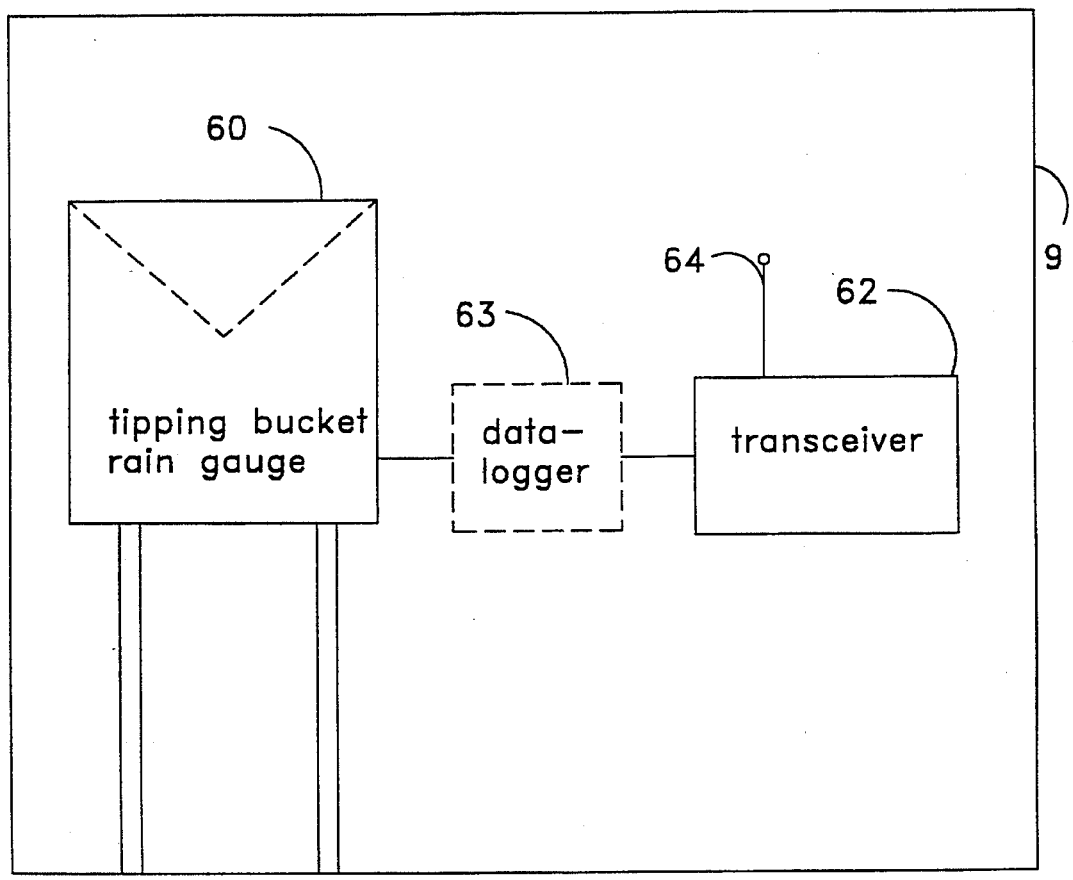
FIG. 3 is a schematic block diagram of a rain gauge station.

Reference is now made to FIG. 3 which is a highly schematic block diagram of a representative embodiment of rain gauge station 9. Rain gauge stations 11 and 13 are similar. Rain gauge station 9 comprises a tipping bucket rain gauge 60, second transceiver 62, and second antenna 64. It may also comprise rain gauge datalogger 63.

Figure 4:
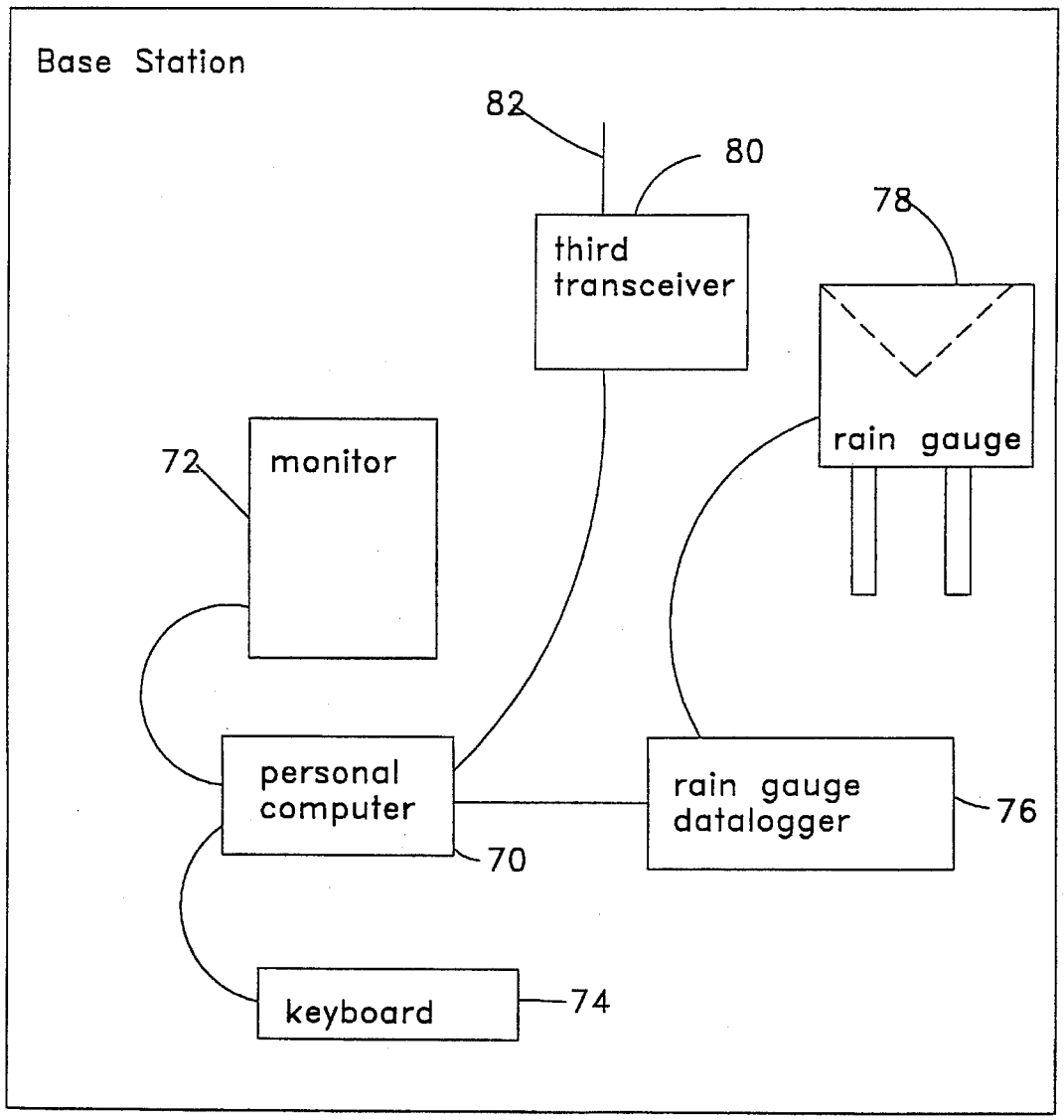
FIG. 4 is a schematic block diagram of a base station.

Reference is now made to FIG. 4 which is a highly schematic block diagram of a representative embodiment of base station 15. Base station 15 comprises microcomputer or personal computer 70, display device or monitor 72, input device or keyboard 74, rain gauge datalogger 76, rain gauge 78, and third transceiver 80 and third antenna 82. Base station 15 may be either permanently located or it may be mobile.

Figure 5:
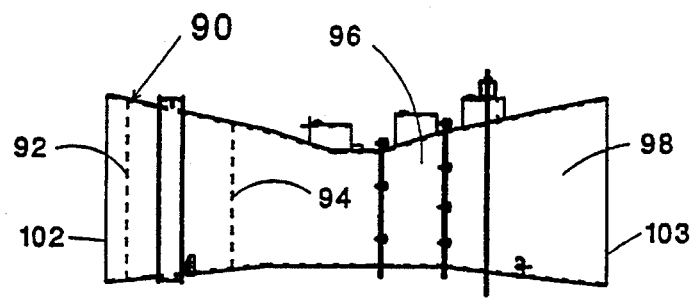
FIG. 5 is a elevation view of a flowtube.
Figure 6:
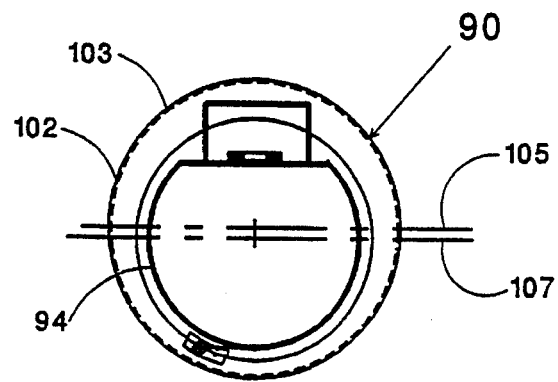
FIG. 6 is a first cross-sectional view of a flowtube.
Figure 7:
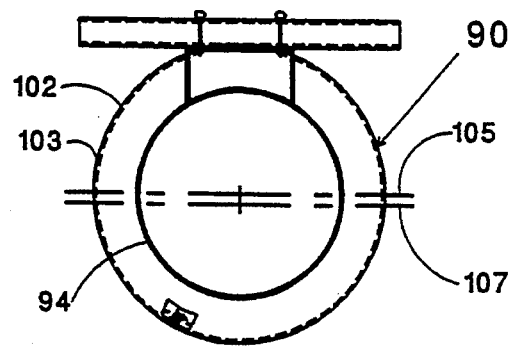
FIG. 7 is a second cross-sectional view of a flowtube.

Reference is now made to FIGS. 5, 6, and 7, which are elevation and cross-section drawings of a preferred embodiment of primary element or flowtube 90. Flowtube 90 comprises entrance section 92 and throat section 94 and may comprise short exit section 96 and extended exit section 98. Flowtube 90 preferably also comprises entrance 102 and may comprise exit 103.

As noted in FIGS. 6 and 7 centerline or longitudinal axis of rotation 105 of entrance 102 and exit 103 is preferably located higher than centerline or axis of rotation 107 of throat section 94. Thus, entrance section 92 and exit section 98 have the shape of an eccentric truncated cone.

In a preferred embodiment, submersible pressure sensors (not shown) are removably attached to mounting fixtures on the outside surface of the flowtube. The submersible pressure sensors are comprised of microelectromechanical devices installed in submessible sensor holders (not shown). Preferably, the microelectromechanical devices are 0–15 pounds per square inch (psi) gauge all media solid state sensor pressure transducers, part type A. (Part No. NPI-19A-101-GH).

In an alternative embodiment, a bubbler pressure sensing and transmitting arrangement is used. The pressure sensors are comprised of microelectromechanical devices mounted in an integrated pneumatic circuit. Preferably, the microelectromechanical devices are 0–1.5 psi differential on-chip temperature compensated and calibrated, silicon piezoresistive pressure sensors. (Part No. MPX 2010D).

Referring to FIG. 1, distributed, unattended wastewater monitoring system 1 operates to monitor the flow rate and/or quality of wastewater flowing in sewers 23, 25, and 27. In one embodiment, sewers 23, 25, and 27 are storm sewers, watercourse 40 is a river, and system 1 is used to accomplish storm water discharge monitoring.

For storm water discharge monitoring, samples are collected from the discharge resulting from a storm event that is greater than 0.1 inches and at least 72 hours from the previously measurable (greater than 0.1 inch rainfall) storm event as measured at rain gauge stations 9, 11, and 13. Where feasible, the variance in the duration of the event and the total rainfall of the event does exceed 50 percent from the average or median rainfall event in the area. A flow-weighted composite is taken for either the entire discharge or for the first three hours of the discharge. The flow-weighted composite samples for storm water discharges may be taken with automatic sampler in flowmeter stations 3, 5, and 7, or as a combination of a minimum of three sample aliquots taken in each hours of the discharge, with each aliquot being separated by a minimum period of fifteen minutes. A minimum of one grab sample is taken form storm water discharges from holding ponds or other impoundments with a retention period greater than 24 hours. For a flow-weighted composite sample, only one analysis of the composite of aliquots is conducted. For storm water discharge samples taken from discharges associated with industrial activities, quantitative data are reported for the grab sample taken during the first thirty minutes (or as soon thereafter as practicable) of the discharge. For all storm water permit applicants taking flow-weighted composites, quantitative data are reported for all pollutants except pH, temperature, cyanide, total phenols, residual chloride, oil and grease, fecal coliform, and fecal streptococcus.

In another embodiment, sewers 23, 25, and 27 are sanitary sewers, sewer 40 is an interceptor sewer and system 1 is used to accomplish wastewater flow monitoring to quantify infiltration/inflow rates. The problems that I/I causes in both large and small wastewater systems are summarized by the Water Pollution Control Federation (Water Pollution Control Federation 1993) Existing sewer evaluation and rehabilitation, Water Pollution Control Fed., Washington, D.C.) as follows:

"Infiltration and inflow seriously affect the operation of sewer systems and pumping, treatment, and overflow regulator facilities. It also adversely affects the urban environment and the quality of water resources. Some examples of the detrimental effects are: usurpation of sewer facility capacity that should be researched for present sanitary wastewater flows and future urban growth; need for construction of relief sewer facilities before originally scheduled dates; surcharging and back-flooding of sewers into streets and private properties; bypassing of raw wastewater at various points of spill or diversion into storm drains or nearby watercourses; surcharging of pump stations, resulting in excessive wear on equipment, higher power costs, or bypassing of flows to adjacent water sources; surcharging of wastewater treatment plants, with adverse consequences to treatment efficiency; diversion of low from secondary-tertiary treatment stages, or bypassing of volumes of untreated wastewater into receiving waters; and increases in the incidence and duration of storm water overflows at combined sewer regulators."

Today, the wastewater industry recognizes that simultaneous, continuous flow monitoring at key points in a sewer system such as at manholes 17, 19, 21, is the only effective way to determine the relative contribution of subsystems to the total problem. Analysis of subsystem flow data can tell the investigator much that can be used to focus subsequent I/I control and sewer rehabilitation activities. In many communities, for example, 70 to 80 percent of the I/I is found to enter only 20 to 30 percent of the collection system (Hunter, R.M. 1984 I/I control comes of age. *Brown and Caldwell Quarterly*, 13(1),6).

Subsystem flow monitoring data can also reveal the magnitude of infiltration and inflow flow rates and flow volumes. Analysis of these data can even tell the investigator the types of sources that are contributing the I/I (Nogaj, R. J. and Hollenbeck, A. J. 1981. One technique for estimating inflow with surcharge conditions. Water Pollut. Control Fed., 53,4.) For these reasons, the ability to obtain accurate wastewater flow measurements is a critical component of state-of-the-art I/I control and sewer rehabilitation programs. This fact has been acknowledged by the U.S. Environmental Protection Agency as follows:

"An effective sewer system evaluation study should be performed in a logical and sequential order. This means that I/I problems should be carefully defined by means of a systematic flow monitoring program(overall subsystem flow monitoring followed by comprehensive flow monitoring and flow isolation within sub-systems) before conducting any other field work. The proposed flow monitoring program should be adequate to allow accurate identification and gradual isolation of sewer sections having excessive I/I . . . " (Longest, H. L. 1980. Infiltration/inflow program-interim policy. Construction grants program requirements memorandum, U.S. Environmental Protection Agency, Washington, D.C.).

WORKING EXAMPLE

Figure 8:
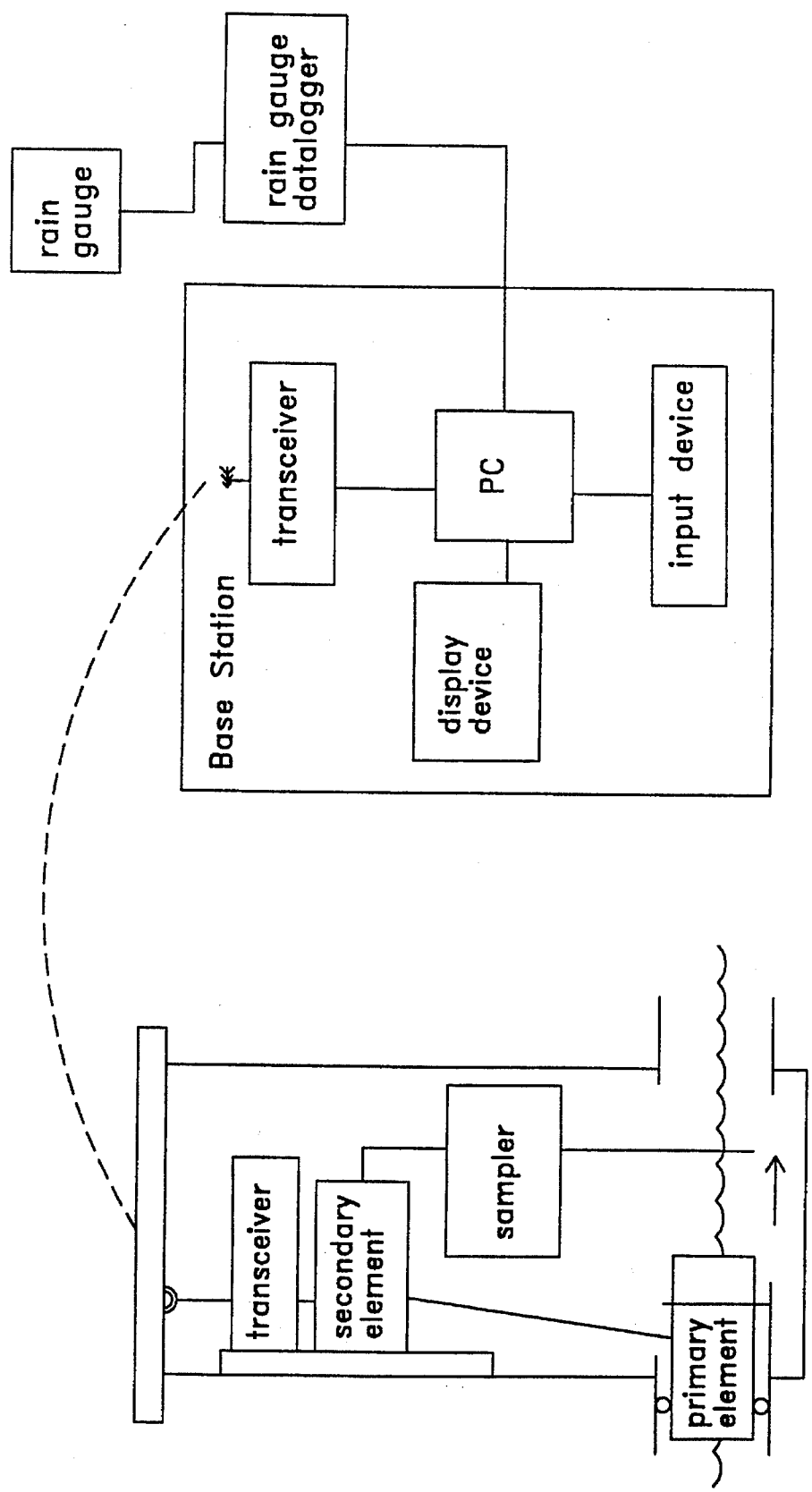
FIG. 8 is a schematic block diagram of a working example of the invention.

A schematic of a working example is shown in FIG. 8. Major components include a sampling unit, a wireless link, a base station/control center, a rain gauge datalogger, and a rain gauge. For commercial applications, the control center may control more than one monitoring subsystem, where each monitoring subsystem consists of a rain gauge and several sampler units, each at a different site. The working prototype consisted of a 24-inch multi-section flowtube fitted with holders for three submersible pressure sensors.

The secondary element included a Campbell-Scientific CR10 datalogger, an interface circuit board, main and backup batteries, a desiccant pack mounted in a NEMA 6P enclosure, three submersible pressure sensors, and a cable harness that included electrical wires and atmospheric pressure, reference vent tubes. Waterproof connectors on the enclosure allowed electrical connections to a sampler, a rain gauge, and an RS-232 device. A vent tube supplied atmospheric reference pressure to the submersible sensors.

The manhole wireless link hardware comprised a Proxlink XR transceiver, a quarter-wave whip antenna, an interface power supply board, a battery pack, and a DC current meter mounted in a splash-proof enclosure. The base station hardware comprised a Proxlink XR transceiver, a power supply, a personal computer, and a rain gauge.

A prototype user-interface/control program was developed in C++ using object-oriented techniques. Interrogation and configuration routines were developed in modular form with a C++ communications library and inserted into the control program after debugging. Compiling was accomplished with a Borland C++ 4.0 compiler.

System monitoring and control was performed by an IBM-compatible personal computer (PC) operating under the Microsoft Windows environment. The PC interfaced with peripheral devices through serial ports COM1 and COM2. The base station transceiver was connected to COM1. This transceiver was adapted to be programmable for either point-to-point or point-to-broadcast mode, allowing it to communicate with either individual or multiple monitoring locations. The base transceiver could contact an individual monitoring site by broadcasting the ID of the site at the beginning of a transmission, or, in a system with multiple sites, the base could contact all the sites simultaneously by broadcasting an ID which all sites recognized. The sampling sites could only transmit to the base station. The working model utilized one monitoring site unit.

PC serial port COM2 was used to communicate with the rain gauge. The working model was configured with the rain gauge located at the base station. The rain gauge consisted of a commercial tipping bucket rain gauge which provides a switch-closure output for each 0.01 inch of rainfall. A Campbell Scientific CR10 datalogger recorded the tip events. The datalogger ran on a software program which computed cumulative rainfall versus time and provided an alarm to the PC if storm water sampling criteria were met. The rain gauge datalogger was connected to the PC with a standard RS-232 cable. The system could also have been configured with a remote stand-alone rain gauge which communicated as a monitoring site. A tipping bucket rain gauge could also have been directly wired to a monitoring site datalogger.

During normal operation, the PC polled each site (including monitoring sites and the rain gauge) at periodic intervals and received a reply to confirm that each site was operational. If a site had collected data since the last communication, the site's reply included a flag that indicated that new data were available. Upon receiving the flag, the base station requested a transmission of all new data from the site (site interrogation). The normal PC screen display was a readout of the status of the system as follows:

Last flow rate record from each monitoring site

Last sample event at each site

Cumulative rain: last hour, day, and total

Maintenance required (change site batteries, change sample bottles, etc).

System errors (failure of a site or rain gauge to respond)

The control software allowed the base station operator to change the operating parameters of any site (site configuration). The user entered this mode by clicking on the Site menu item. Parameters which could be modified during a study included baseline flow, flow interval between samples, time interval between samples, time interval between flow rate measurements, and sampling mode (time or flow proportional). The user could interrogate a site to determine its current operating parameters.

Data from each site and from the rain gauge were stored in persistent-memory databases on the PC hard drive. This data could be displayed on screen, copied to printer, or exported to disk. Data were appended to the appropriate database each time new records were received from a site.

Tests of the working model were conducted with the following objectives:

1. To determine if reliable data communication was possible with a device located in a manhole, using license-free radio technology.
2. If communication was possible, to determine if the power requirements were compatible with use of a portable battery pack.

A pair of 500 milliwatt (maximum output power) spread-spectrum transceivers were used during one set of tests. (This is the same frequency band as is used by two-way pagers.) One of the units was placed in a sewer manhole, and the other unit was placed 25 feet away from the manhole. A 0 to 100 decibel (db) variable attenuator was installed between the manhole unit and its antenna to reduce the effective transmission power. Tests were conducted to determine the transmission power requirements of the manhole transceiver with various combinations of manhole antenna depth and orientation. A second set of tests was conducted to determine the effects of a pick hole in the manhole cover. A third set of tests was conducted to determine the effect of a vehicle located between the two transceivers.

Based on the results of these tests, a best-case scenario was simulated. The best-case conditions consisted of a standard 24 inch cast-iron manhole cover in place over the manhole. The cover had a standard approximately 1-inch diameter hole through it. There were no objects blocking the transmission path between the manhole cover and surface transceiver. The manhole unit used a 3-inch whip antenna taped across the hole on the bottom side of the cover. The surface unit used a directional Yagi antenna mounted 4 feet above ground level, pointed at the manhole. Communication between the units was achieved with up to 40 dB of attenuation, which is equivalent to a transmission power of 50 microwatts (0.05 milliwatts) under the best-case conditions. Most of the signal was radiated through the hole in the cover.

Additional experiments determined that communication was severely impaired by blocking the hole in the manhole cover or by placing a vehicle so that it blocked the line of site between the two transceivers. Since a commercial system would be likely to experience one or both of these adverse conditions, worst-case experiments were conducted with a steel plate blocking the hole and a pickup truck parked between the manhole cover and surface unit antenna. The most effective antenna system for the manhole unit was fabricated by electrically coupling the coaxial antenna cable to the lower side of the cover through an iron magnet bolted to the terminal end of the cable. Communication was achieved under these worst-case conditions with a maximum attenuation of 20 dB, which is equivalent to a transmission power of 5 milliwatts.

A pair of 433 mHz narrow-band transceivers were used for conventional FM radio tests. The surface unit had an output power of 5 milliwatts, and the manhole unit had an output power of 10 milliwatts. The manhole unit antenna was a 6-inch whip device which was taped flat to the lower side of the cover. Tests indicated that the 10 milliwatt signal was received effectively under the previously described worst-case conditions. The 5-milliwatt signal was intermittently received.

Figure 9:
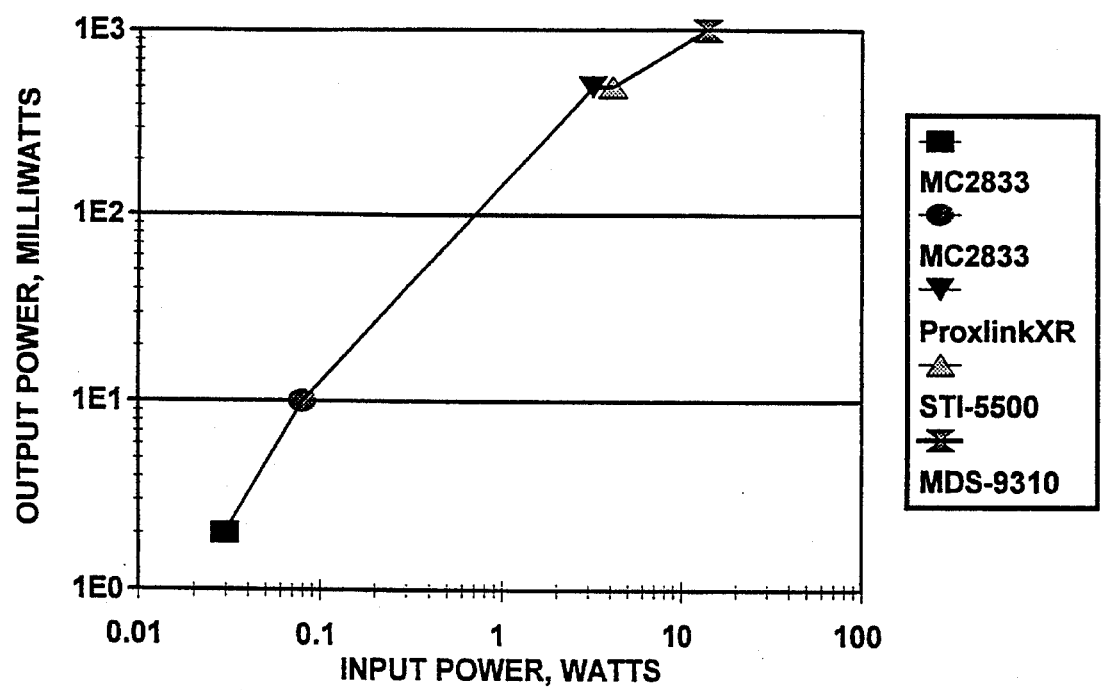
FIG. 9 is a plot of the output power versus the input power of available FM transmitters.

The essentially linear relationship between input power and output power for commercially-available FM transmitters is illustrated in FIG. 9. This graph was used to estimate the expected battery drain for an efficient 10-milliwatt transmitter. Calculations indicated that a battery pack consisting of eight D-cell alkaline batteries would have a life of at least 14 days at 70° F. while powering a 10-milliwatt transmitter, a receiver, and a datalogger. This scenario assumed that the transceiver is continuously active, and that receive mode required the same power as transmit mode (a conservative assumption for currently available devices). Significant power savings would be expected if timing and switching circuitry were employed for transceiver control.

We claim:

1. A system for monitoring a flowing wastewater comprising:

at least one flowmeter station installed in a sewer manhole, said at least one flowmeter station comprising a secondary element and a first wireless transmitter/receiver, and said sewer manhole having a cover, said first wireless transmitter/receiver being attached to said secondary element of each said at least one flowmeter station, having a first antenna, and being adapted to transmit and receive radio signals through said manhole cover, said signals being characterized by a first transmission power value, and a base station comprising a second wireless transmitter/receiver and a computer, said second wireless transmitter/receiver having a second antenna and being adapted to transmit and receive radio signals through said manhole cover, said signals being characterized by a second transmission power value, wherein said first and second transmission power values are selected from the group consisting of
at least 0.05 milliwatts when said cover has at least one standard hole, and
at least 5 milliwatts when said cover is holeless.

2. The system of claim 1 wherein a first antenna cable is attached to said first wireless transmitter/receiver and said first antenna cable is attached by means of a magnet to said cover.

3. The system of claim 1 wherein said cover acts as said first antenna.

4. The system of claim 1 further comprising an automatic sampler attached to and actuated by said secondary element.

5. The system of claim 1 wherein said base station further comprises an attached rain gauge.

6. The system of claim 1 further comprising at least one rain gauge station comprising a rain gauge and a wireless transmitter having a third antenna and being adapted to transmit radio signals.

7. The system of claim 1 further comprising a relay station adapted to relay radio signals between said at least one flowmeter station and said base station.

8. The system of claim 1 wherein said at least one flowmeter station further comprises a primary element and said primary element comprises a constriction having an entrance section and a throat section, wherein said entrance section has a shape that is an eccentric, truncated cone.

9. The system of claim 8 wherein said primary element produces pressures in the wastewater and said pressures are sensed by microelectromechanical devices.

10. A method for monitoring a flowing wastewater comprising:

installing at least one flowmeter station in a sewer manhole, said at least one flowmeter station comprising a secondary element and a first wireless transmitter/receiver, and said sewer manhole having a cover, said first wireless transmitter/receiver being attached to said secondary element of each said at least one flowmeter station, having a first antenna, and being adapted to transmit and receive radio signals through said manhole cover, said signals being characterized by a first transmission power value, and providing a base station comprising a second wireless transmitter/receiver and a computer, said second wireless transmitter/receiver having a second antenna and being adapted to transmit and receive radio signals through said manhole cover, said signals being characterized by a second transmission power value, wherein said first and second transmission power values are selected from the group consisting of
at least 0.05 milliwatts when said cover has at least one standard hole, and
at least 5 milliwatts when said cover is holeless.

11. The method of claim 10 wherein a first antenna cable is attached to said first wireless transmitter/receiver and said first antenna cable is attached by means of a magnet to said cover.

12. The method of claim 10 wherein said cover acts as said first antenna.

13. The method of claim 10 further comprising attaching an automatic sampler to and actuating said sampler by said secondary element.

14. The method of claim 10 wherein said base station further comprises an attached rain gauge.

15. The method of claim 10 further comprising providing at least one rain gauge station comprising a rain gauge and a wireless transmitter having a third antenna and being adapted to transmit radio signals.

16. The method of claim 10 further comprising providing a relay station adapted to relay radio signals between said at least one flowmeter station and said base station.

17. The method of claim 10 wherein said at least one flowmeter station further comprises a primary element and said primary element comprises a constriction having an entrance section and a throat section, wherein said entrance section has a shape that is an eccentric, truncated cone.

18. The method of claim 17 wherein said primary element produces pressures in the wastewater and said pressures are sensed by microelectromechanical devices.

19. A system for monitoring a flowing wastewater comprising:

at least one flowmeter station installed in a sewer manhole, said at least one flowmeter station comprising a secondary element and a first wireless transmitter/receiver, and said sewer manhole having a cover that is in place, said first wireless transmitter/receiver being attached to said secondary element of each said at least one flowmeter station, and having a first antenna, and a base station comprising a second wireless transmitter/ receiver and a computer, said second wireless transmitter/receiver having a second antenna, wherein data are communicated between said flowmeter station and said base station by means of radio signals produced by said wireless transmitter/receivers.

20. The system of claim 19 wherein said first and second wireless transmitter/receivers are adapted to transmit and receive said radio signals through said manhole cover.

21. A method for monitoring a flowing wastewater comprising:

installing at least one flowmeter station in a sewer manhole, said at least one flowmeter station comprising a secondary element and a first wireless transmitter/ receiver, said sewer manhole having a cover that is in place, said cover having a hole therein, said first wireless transmitter/receiver being attached to said secondary element of each said at least one flowmeter station, and having a first antenna, and providing a base station comprising a second wireless transmitter/receiver and a computer, said second wireless transmitter/receiver having a second antenna, wherein data are communicated between said flowmeter station and said base station by means of radio signals produced by said wireless transmitter/receivers.

22. The method of claim 21 wherein said first and second wireless transmitter/receivers are adapted to transmit and receive said radio signals through said hole.

* * * * *